US010060854B2

(12) United States Patent
Schortgen (10) Patent No.: US 10,060,854 B2
(45) Date of Patent: Aug. 28, 2018

(54) NON-INVASIVE DEVICE FOR DETERMINING THE FERTILITY AND/OR THE SEX OF AN EGG, AND CORRESPONDING METHOD

(71) Applicant: TRONICO, Saint Philbert de Bouaine (FR)

(72) Inventor: Marc Schortgen, Domagne (FR)

(73) Assignee: TRONICO, Saint Philbert de Bouaine (FR)

( * ) Notice: Subject to any disclaimer, the term of this patent is extended or adjusted under 35 U.S.C. 154(b) by 0 days.

(21) Appl. No.: 15/325,646

(22) PCT Filed: Jul. 9, 2015

(86) PCT No.: PCT/EP2015/065778
§ 371 (c)(1),
(2) Date: Jan. 11, 2017

(87) PCT Pub. No.: WO2016/005539
PCT Pub. Date: Jan. 14, 2016

(65) Prior Publication Data
US 2017/0160202 A1 Jun. 8, 2017

(30) Foreign Application Priority Data

Jul. 11, 2014 (FR) ...................................... 14 56744

(51) Int. Cl.
*G01N 21/65* (2006.01)
*G01N 33/08* (2006.01)

(52) U.S. Cl.
CPC ............. *G01N 21/65* (2013.01); *G01N 33/08* (2013.01); *G01N 2201/06113* (2013.01); *G01N 2201/08* (2013.01); *G01N 2201/12* (2013.01)

(58) Field of Classification Search
None
See application file for complete search history.

(56) References Cited

U.S. PATENT DOCUMENTS

| 6,029,080 A | 2/2000 | Reynnells et al. |
| 8,624,190 B2 | 1/2014 | Steiner et al. |
| (Continued) | | |

FOREIGN PATENT DOCUMENTS

| DE | 102012023947 B4 * | 11/2016 | ............. G01N 33/08 |
| WO | 2014021715 A2 | 2/2014 | |
| WO | WO 2014086335 A9 * | 7/2014 | ............. G01N 33/08 |

OTHER PUBLICATIONS

International Search Report dated Sep. 24, 2015 for corresponding International Application No. PCT/EP2015/065778, filed Jul. 9, 2015.

(Continued)

*Primary Examiner* — Shawn Decenzo
(74) *Attorney, Agent, or Firm* — David D. Brush; Westman, Champlin & Koehler, P.A.

(57) ABSTRACT

A non-invasive device for determining the fertility and/or sex of an egg. This device obtains a spectral response, specific to the shell, to an incident light signal. The device has a focusing element configured to focus the incident light signal on a surface portion and/or an internal portion of at least one layer of the shell, and elements for determining the fertility and/or sex of the egg as a function of the spectral response specific to the shell.

10 Claims, 5 Drawing Sheets

(56) References Cited

U.S. PATENT DOCUMENTS

| | | | | |
|---|---|---|---|---|
| 9,835,560 | B2* | 12/2017 | Galli | G01N 21/65 |
| 2002/0075476 | A1 | 6/2002 | Chalker, II et al. | |
| 2011/0144473 | A1 | 6/2011 | Opitz et al. | |
| 2012/0058052 | A1* | 3/2012 | Decuypere | A01K 45/00 |
| | | | | 424/9.6 |
| 2012/0318981 | A1* | 12/2012 | Steiner | A01K 45/007 |
| | | | | 250/339.07 |
| 2013/0044210 | A1* | 2/2013 | Rozenboim | G01N 21/31 |
| | | | | 348/135 |
| 2015/0337372 | A1* | 11/2015 | Winger | G01N 33/08 |
| | | | | 506/9 |
| 2016/0050891 | A1* | 2/2016 | Phelps | A01K 45/00 |
| | | | | 73/863.21 |

OTHER PUBLICATIONS

English translation of the Written Opinion of the International Searching Authority dated Nov. 29, 2016, for corresponding International Application No. PCT/EP2015/065778, filed Jul. 9, 2015.

L. Liu et al., "Detecting Fertility and Early Embryo Development of Chicken Eggs Using Near-Infrared Hyperspectral Imaging", Food and Bioprocess Technology, vol. 6, No. 9, Aug. 2, 2012 (Aug. 2, 2012), pp. 2503-2513, XP055173098.

Gerald Steiner et al., "Gender Determination of Fertalized Unincubated Chicken Eggs by Infrared Spectroscopic Imaging", Analytical and Bioanalytical Chemistry, Springer, Berlin, DE, vol. 400, No. 9, Apr. 9, 2011, pp. 2775-2782, XP019909218.

\* cited by examiner

NON-INVASIVE DEVICE FOR DETERMINING THE FERTILITY AND/OR THE SEX OF AN EGG, AND CORRESPONDING METHOD

1. CROSS-REFERENCE TO RELATED APPLICATIONS

This Application is a Section 371 National Stage Application of International Application No. PCT/EP2015/065778, filed Jul. 9, 2015, the content of which is incorporated herein by reference in its entirety, and published as WO 2016/005539 on Jan. 14, 2016, not in English.

2. FIELD OF THE INVENTION

The field of the invention is that of poultry farming.

More particularly, the invention relates to a non-invasive technique for determining the fertility of an egg and/or its sex (i.e. determining whether the embryo contained in an egg, if fertilized, is male or female).

3. TECHNOLOGICAL BACKGROUND

For many years now, there have been problems in the poultry-farming sector with regard to determining the fertility and sex of eggs before they are hatched.

Traditionally, sexing is done on a day-old chick by human intervention, chiefly via two techniques: feather sexing by observation of the feathers and vent sexing by observation of the vent.

Although these methods are efficient, their major drawback is that they come into operation too late in the production cycle. For example, in the case of laying hens, 21 days of incubation are needed to separate the females from the males (the latter are eliminated).

Determining the sex of embryos at an early stage of incubation would improve poultry farm production, with gains both in time and in financial profit.

A certain number of more or less invasive techniques have therefore been developed for determining and assessing the fertility and sex of a bird's not-hatched egg.

A first known technique is described in the U.S. Pat. No. 6,029,080, which proposes a method of determination by nuclear magnetic resonance. This technique is used to sort out the eggs into three categories: eggs containing male embryos, those containing female embryos and non-fertilized or "clear" eggs. The sorting is done by observation of the reproductive organs through the shell. More particularly, the observation can be done only after freezing the egg in order to minimize the movements of the embryo. One drawback of this technique is that the freezing of the egg causes disturbance in the future development of the embryo. Another drawback is that implementing such a technique is relatively costly. This acts as a brake on its industrial-scale development.

A second known technique is described in the patent application US2011/0144473, which describes the use of UV spectroscopy. This technique consists in sending out a wave in the ultraviolet domain so as to prompt auto-fluorescence in a region of the germinal disc (the blastodisc). To determine the sex of the embryo, a coefficient of decrease is computed and then compared with the database following the observation of the decrease of auto-fluorescence after the emission of the UV wave has been stopped. However, one drawback of this technique is that it requires access to the blastodisc by invasive removal.

A third known technique is based on infrared spectroscopy. This method which is also invasive consists of the introduction of a probe into the germinal disk region in order to characterize its constituent cells by infrared spectroscopy.

One major drawback of the second and third prior art techniques is that they are invasive: they require the introduction of instruments and the removal of cells from the germ. These operations are therefore not without risk for the future development of the embryo. Another drawback of these two techniques is the risk of contamination of the entire brood.

In order to overcome this major drawback, a fourth, non-invasive, prior art technique is described in the patent application US2013/0044210. It consists of a hyperspectral analysis (i.e. analysis from the mid-infrared to the near-UV) of an optical spectrum in reflection from the egg, in subtracting the spectral response of the shell and detecting the biological components of the egg. This technique can determine whether the egg is fertilized as of the second day and the sex of the embryo on the twelfth day. One major drawback of this technique is that it requires corrections to compensate for the shell (by subtracting its spectral response) and for environmental disturbances (light, humidity, etc.). To this end, each egg must be placed on a specific support maintaining a known distance between the radiation source, the detector and the egg. This technique is therefore difficult to carry out on an industrial scale.

Owing probably to the above-mentioned drawbacks, none of the prior art techniques cited above have truly led to industrial-scale development.

4. SUMMARY OF THE INVENTION

An exemplary embodiment of the present disclosure is directed to a non-invasive device for determining the fertility and/or sex of an egg.

According to the invention, said device comprises means for obtaining a spectral response, specific to a shell (i.e. a shell-specific spectral response), to an incident light signal, the device comprising focusing means adapted to focusing said incident light signal on a surface portion and/or an internal portion of at least one layer of the shell, and means for determining the fertility and/or sex of the egg as a function of said spectral response specific to a shell (or shell-specific spectral response).

The general principle of the invention therefore consists in obtaining a shell-specific spectral response to an incident light signal and determining the fertility and/or sex of the egg according to this spectral response.

To this end, the invention therefore implements particular focusing means used to focus the incident light signal on the surface and/or on an internal portion of a very precise layer of the shell to be examined.

Thus, this particular embodiment of the invention relies on a wholly novel and inventive approach to the non-invasive determining of the fertility and/or sex of an egg since it relies on spectroscopy of the surface and/or of an internal portion of a layer of the eggshell. Indeed, as described in detail further below, the inventors have put forward the hypothesis according to which the discriminant substances existing in all the cells of the embryo and playing a role in sexual differentiation are not concentrated uniquely in the gonads but are spread throughout the egg though the allantoic fluid and can, in a minute but measureable proportion, be present on the surface and inside the shell.

It may be recalled that the fourth prior art technique (the only non-invasive technique known to the inventors) seeks on the contrary to do without the spectral response of the shell by removing it from that of the egg so as to keep only the spectral response of the contents of the egg (comprising the albumen, the yolk and the germinal disc).

The incident light signal is either a mono-wavelength light signal (i.e. having a single wavelength) or a multi-wavelength light signal having at least two wavelengths (successively or simultaneously).

According to one particular characteristic, the incident light signal comprises at least one wavelength ranging from 200 to 1100 nm.

These wavelengths enable optimum functioning.

According to one particular aspect, the focusing means are adapted to focusing the incident light signal on a portion of the external surface of an external layer of the shell.

The advantage of focusing on the surface of the shell is that the reflected signal (for example reflected Raman signal) is of higher value, since the absorption is lower.

According to one particular aspect, the focusing means comprise a probe having a focusing distance D relative to a lens and an end-piece, a first extremity of which is fixedly attached to the probe and placed at a distance d1 from the lens and a second extremity of which is intended to be in contact with the egg, the end-piece having a distance d2 between the first and second extremities with d2=D−d1.

Such an end-piece therefore enables the probe to be always at the same distance from the surface of the egg. In other words, the end-piece enables easy adaptability of the device to all sizes of eggs without additional adjustment. It is therefore naturally possible to envisage the industrial-scale application of such a device.

Since the distance between the lens of the probe and the egg is fixed by the end-piece calibrated in length, the focusing distance D can easily be adjusted by modifying the wavelength of the incident light signal. Such an aspect also enables high precision for the device. In addition, the adjustment and the maintenance of such a device are made easier since only the wavelength is considered to be variable.

According to one particular aspect, the means used for obtaining the spectral response comprise a probe, or said probe, adapted to transmitting the incident light signal towards the egg, and to receiving, at a zero angle of reflection, a reflected light signal resulting from a reflection by the egg of the incident light signal.

In this way, even if the reflected light signal is relatively weak, such a probe ensures and optimizes the recovery of the reflected signal.

In one particular embodiment of the invention, the probe is a Raman type probe.

Such a probe enables high precision in the transmission of the incident signal and in the reception of the reflected signal.

In one particular embodiment of the invention, the means for obtaining the spectral response specific to the shell comprise:
- an attenuated total reflection probe comprising a crystal that receives an incident light signal and generates a reflected light signal;
- a spectrometer that recovers the reflected light signal generated by said probe, and
- processing means configured to obtain the shell-specific spectral response as a function of said incident light signal and of said reflected light signal.

Such means for obtaining the shell-specific spectral response enable the probe to be always at the same distance from the surface of the egg since the crystal of the ATR probes is in contact with the sample to be studied. This aspect enables easy adaptability of the device to all sizes of eggs without additional adjustment.

During this spectroscopy, a part of the incident signal is absorbed by the shell thus attenuating the reflected signal. Since the spectral response of the incident signal is known and the spectral response of the incident signal is measured with precision by the spectrometer, the spectral response specific to the eggshell can be deduced easily by the processing means through the subtraction of the spectral response of the reflected signal from the spectral response of the incident signal. In other words, this spectral response specific to the shell corresponds to the spectral response of the signal attenuated by the shell.

According to one particular aspect of the invention, the means for determining the fertility and/or sex of the egg comprise means for comparing the spectral response obtained with at least one reference spectral response.

Such a comparison facilitates the determining of the fertility and/or sex of the egg. Indeed, the comparison means make it possible to avoid a precise determining of the discriminant substances present while enabling a comparison of the general aspect of the spectrum obtained with that of one or more reference spectra.

According to one particular aspect of the invention, said at least one reference spectral response belongs to the group comprising:
- a first reference spectral response for non-fertilized eggs;
- a second reference spectral response for fertilized eggs containing dead embryos;
- a third reference spectral response for fertilized eggs containing male embryos; and
- a fourth reference spectral response for fertilized eggs containing female embryos.

The invention also relates to a non-invasive method for determining the fertility and/or sex of an egg comprising a step for obtaining a spectral response from at least one portion of at least one a layer of the shell to an incident light signal and a step for determining the fertility and/or sex of the egg as a function of the spectral response obtained.

5. LIST OF FIGURES

Other features and advantages of the invention shall appear from the following description, given by way an indicatory and non-exhaustive example, and from the appended drawings, of which.

6. DETAILED DESCRIPTION OF TWO EMBODIMENTS

6.1 Basic Principles

In all the figures of the present document, the identical steps and elements are designated by a same numerical reference.

The inventors have based their conclusions on several observations, namely:
1. The sexual differentiation of the embryo does not result essentially from the action of the hormones on the gonads.
2. The somatic cells have an independent sexual identity.
3. The main substances taking part in the female determination comprise:
    a. proteins such as FOXL2 involved in the maintenance of the ovary function;
    b. estrogens such as estradiol secreted by the ovary of the embryo;
    c. enzymes such as MHM or Aromatase (CYP19A1) which helps in the conversion of steroid hormones into estrogen;
    d. genetic material such as the gene HINTW (or WPKCI) present in several female embryo tissues as well as the genes DAX1, WNT4, FET1.
4. The main substances participating in male determination comprise:
    a. hormones such as AMH responsible for the regression of the female upper genital passages;
    b. genetic material such as the gene DMRT1 which plays a part in the formation of testicles or SOX9 taking part in the formation of gonads.

The above-mentioned substances (here below also called discriminant substances) are of different types:
  degradation products derived from biosynthesis, such as aromatase which indicates the presence of steroids, the hormone AMH present in allantoic fluid in greater quantities for the female embryo than for the male embryo, the MHM enzyme or the HINTW gene;
  steroids such as estradiol are also present in the allantoic fluid.

The inventors have put forward the hypothesis that these discriminant substances, which exist in all cells of the embryo and play a role in sexual differentiation, are not concentrated exclusively in the gonads but get diffused in the egg by means of the allantoic fluid and can, in a minute but measurable proportion, either migrate towards and through the shell (during the discharge of water vapor or $CO_2$) or get fixed in the shell. Depending on their size they are found either on the surface of the shell or encrusted in the shell (for example in the shell membranes).

Figure 1:
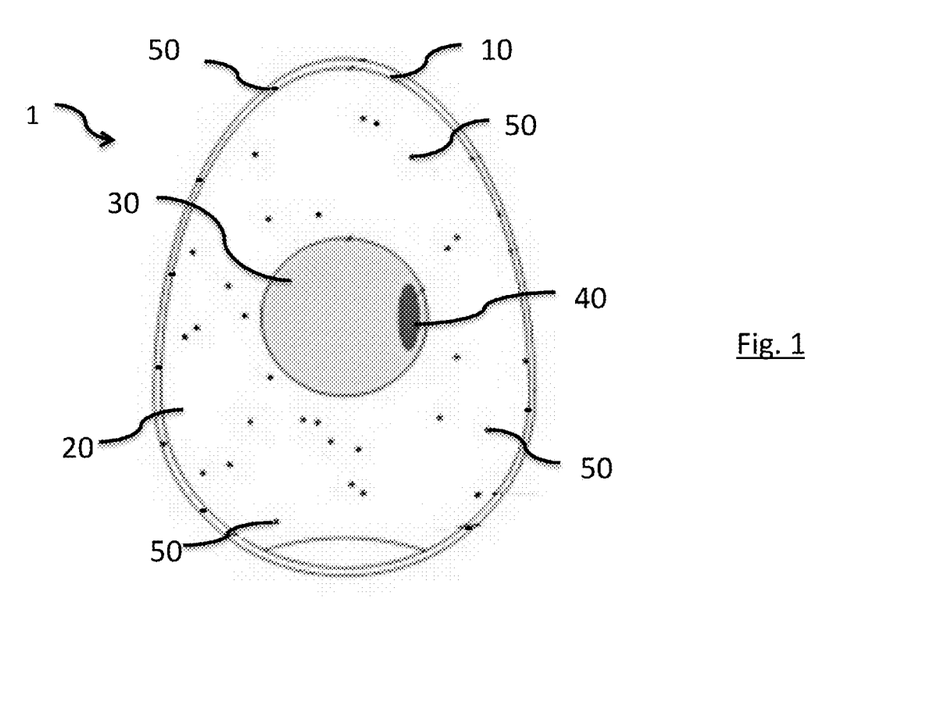
FIG. 1 shows the simplified structure of a fertilized egg.

As illustrated in FIG. 1, an egg comprises a shell 10 and internal contents themselves comprising albumen 20, the yolk 30 and the germinal disc 40.

Figure 2:
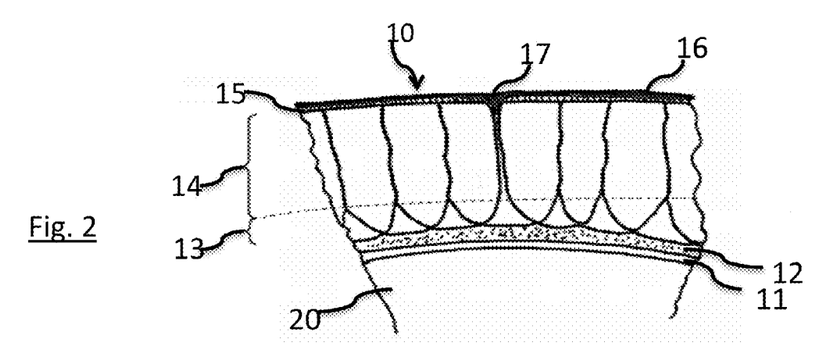
FIG. 2 is a view in section of a structure of the shell of an egg.

As illustrated in FIG. 2, the shell 10 has a superimposition of six layers, namely (starting from the albumen 20): the internal shell membrane 11, the external shell membrane 12, the mammillary layer 13, the palisade layer 14, traversed by pores 17, a monolayer of vertical crystals (15) and finally the cuticule 16 enveloping all the mineral layers.

As indicated above and illustrated in FIG. 1, a plurality of discriminant substances 15 are present not only in the internal layer (and more specifically in the albumen 20) but also on the surface and/or interior of the shell 20. Although small, the presence and quantity of these discriminant substances 50 on the surface and/or in the shell 20 can be measured by spectroscopy.

6.2 Description of a First Embodiment

Figure 3:
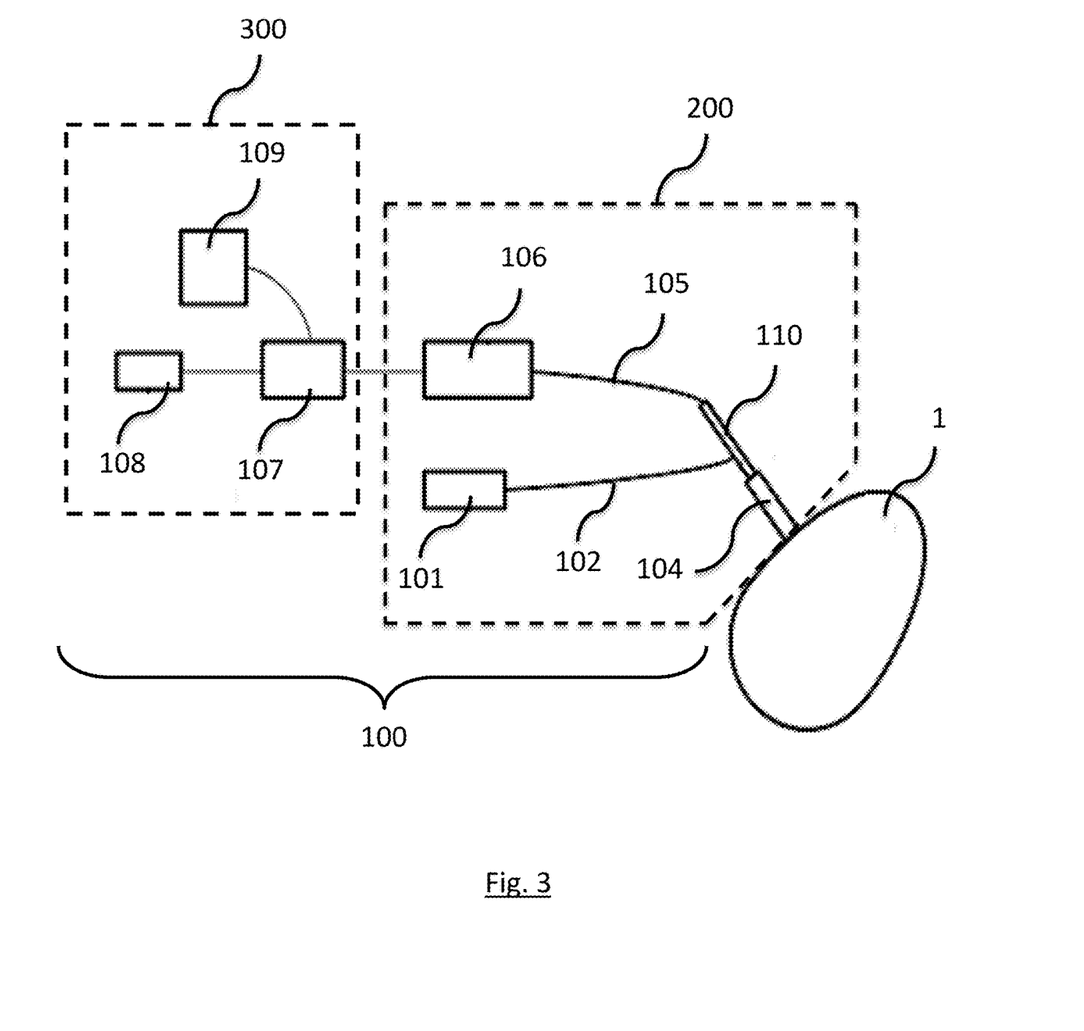
FIG. 3 presents a device for determining the fertility and/or sex of an egg according to a first embodiment of the invention.

Referring now to FIG. 3, we present a device 100 for determining the fertility and/or sex of an egg according to a first particular embodiment of the invention.

Raman spectroscopy is a technique of non-destructive analysis used to characterize the molecular composition of the structure of a material. This technique is based on the detection of the inelastically scattered photons following the interaction of the sample with a beam of monochromatic light (Raman scattering). The difference in frequency between the exciting photon and the reflected photon provides information on the chemical nature of the substance (the molecule) that has caused the scattering. In other words, Raman scattering is the physical phenomenon through which a medium is capable of slightly modifying the frequency of the light that flows therein. This frequency shift corresponds to an exchange of energy between the light ray and the medium. This exchange can have several causes: vibrations of the crystal or of the molecule, magnetic excitation, etc. The measurement of this shift makes it possible to trace the phenomenon back to certain properties of the environment.

In the particular embodiment described below, Raman spectroscopy is used to determine the fertility and/or sex of an egg. It is clear however that the present invention is not limited to this type of spectroscopy but can be implemented with any technique that can be used to obtain the spectral response of at least one portion of at least one layer of the shell. The second embodiment described further below is an example of this.

The general principle of the proposed technique is the following: a small surface of the shell receives at least one incident electromagnetic wave of a defined length. According to the technique employed, the spot generated (here below called the focal point or focusing area) will have for example a diameter of a few microns to 150 microns.

The greater part of the incident wave is reflected at the same frequency and a minute part of the incident wave is reflected at different frequencies. Depending on the type of spectroscopy used, either one of the reflected waves is used.

In the embodiment presented, the device 100 comprises:
  means 200 for obtaining a spectral response specific to the shell 10 of an egg 1. These means 200 comprise a light source 101, a first optical fiber 102, a probe 110, an end-piece 104, a second optical fiber 105 and a spectrometer 106;
  means 300 for determining the fertility and/or the sex of the egg 1 as a function of the spectral response specific to the shell 10. These means 300 comprise a computer 107, a database 109 and a display unit 108.

The light source 101 is for example a laser capable of giving an incident light signal. More particularly, the light signal given by the laser 101 is for example an electromagnetic wave with a single wavelength, preferably situated between 200 and 1100 nm (and again more preferably between 500 and 700 nm).

In one variant (multi-wavelength spectroscopy), the incident light signal is a multi-wavelength signal with at least two wavelengths (successive or simultaneous) each between 200 and 1100 nm. This variant makes it possible to obtain a more complete spectrum and therefore more reliable results. It also removes the need for fluorescence.

The probe 110 and the end-piece 104 together form a focusing means. The first optical fiber 102 is intended to transmit the incident light signal to the probe 110.

The end-piece 104 is calibrated in length and fixedly attached to the probe 110. It enables the probe 110 to be situated at a constant distance from the egg 1. A first extremity of the end-piece 104 is fixedly attached to the probe 110 and a second extremity of the end-piece 104 is to come into contact with the egg 1.

Since the response of the light signal reflected by the surface of the shell 10 of the egg 1 is relatively small, the probe 110, in one particular embodiment, is adapted to recovering the reflected signal in the same axis as the incident signal. This type of probe is more commonly known as a Raman probe.

Figure 4:
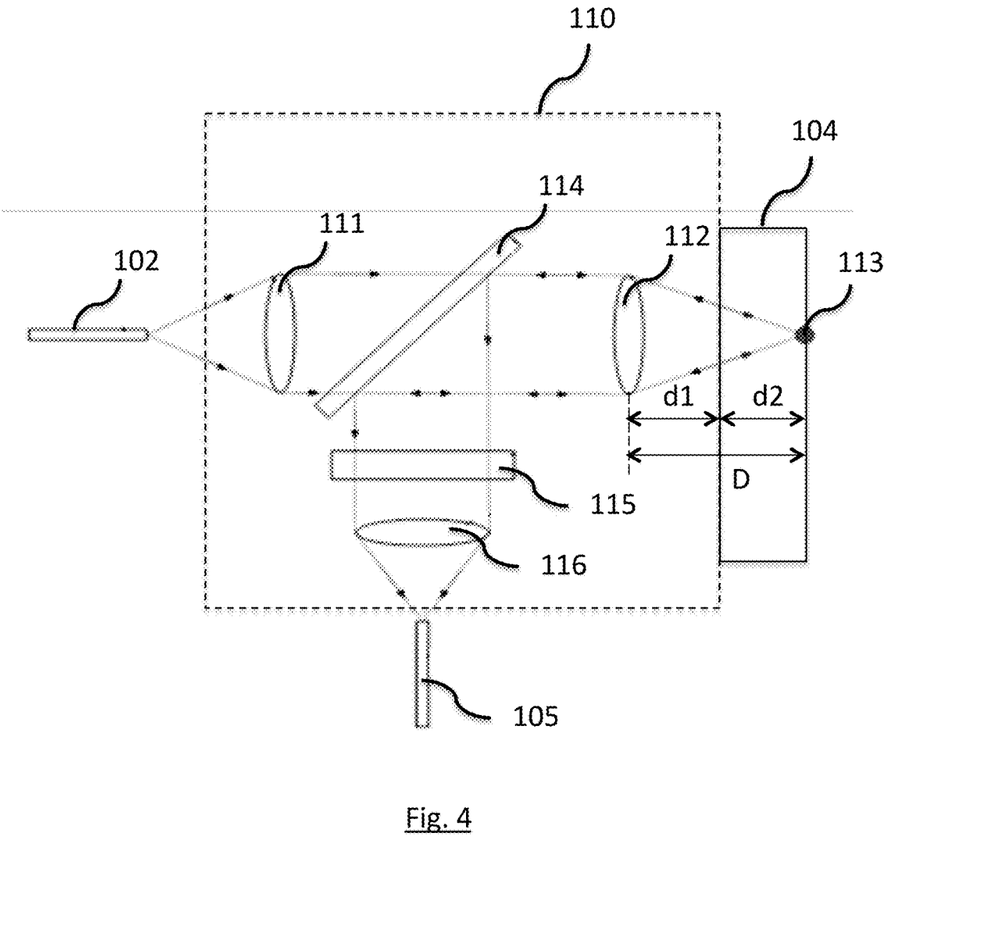
FIG. 4 is a detailed view of the functioning of the probe of the device of FIG. 3.

The principle of operation of such a Raman probe 110 is illustrated in FIG. 4. The incident light signal coming from the first optical fiber 102 is collimated by means of a first lens 111. A collimated light is a light, the rays of which are substantially parallel and are deployed slowly when they get propagated. In other words, it is a light that does not get dispersed with distance (in theory) or which will be dispersed to a very small extent (in practice). This collimated signal is then focused by means of a second lens 112 on a focal point or focusing area 113 situated on the surface or inside the shell 10 to be examined. The focal point 113 is also called a spot.

Since the first and second lenses (111, 112) are fixed, the focusing distance can be modified only by variation of the wavelength of the incident light signal. Here, the focusing distance D of the probe 110 will be defined as the distance between the second lens 111 and the spot 113.

In one particular implementation (illustrated in FIG. 3), the spot 113 is situated on the external surface of the external layer 16 of the shell 10. To this end, the length d2 of the end-piece 104 is obtained according to the formula: d2=D−d1, with d1 being the distance between the first extremity of the end-piece 104 (fixedly attached to the probe 104) and the lens 112. A second extremity of the end-piece 104, situated at the distance d2 from the first extremity, is to come into contact with the external surface of the egg.

In this particular implementation, the incident light signal is reflected (by the portion of the surface of the egg that corresponds to the spot 113) and the reflected signal is collected/collimated by the same lens 112 then directed by means of a dichroic mirror 114 to the spectrometer 106.

In order to optimize the signal received by the spectrometer 106, the signal directed by means of a dichroic mirror 114 passes preliminarily though a high-pass optical filter 115 intended to eliminate the Rayleigh scattering, is then focused by a third lens 116 and is finally transmitted to the spectrometer 106 by the second optical fiber 105.

The spectrometer 106 analyses the received signal and gives a spectral response to the means 300 for determining the fertility and/or sex of the egg 1.

Within the means 300 for determining the fertility and/or sex of the egg 1, the computer 107 and database 109 form comparison means. These means are used to exploit the spectral response transmitted by the spectrometer 106 and compare it with a library of reference spectral responses. This comparison relates either to the amplitude of one or more lines of the spectral response or to the aspect of the entire spectral response.

One particular embodiment uses the four following spectral reference responses:
   a first reference spectral response for the non-fertilized eggs;
   a second reference spectral response for the fertilized eggs containing dead embryos;
   a third reference spectral response for the fertilized eggs containing male embryos;
   a fourth reference spectral response for the fertilized eggs containing female embryos.

In one variant, the group of non-fertilized eggs and that of fertilized eggs containing dead embryos can be grouped in one and the same group. In other words, the first and fourth reference spectral responses are one and the same reference spectral response.

The display unit 108 enables the display of the spectral response obtained as well as the result of the comparison of this spectral response with the database of the reference spectral responses.

Obtaining the database 109 comprises for example the following steps:
   Step 1: on a batch ("configuration batch"), a Raman spectrum (spectral response of the shell according to the technique described above with reference to FIGS. 3 and 4) is read on each egg one different days of incubation;
   Step 2: a correlation is made in order to determine the zones that differ from one spectrum to another (determining zones). This method is used to classify the spectra into categories (reference spectral responses).
   Step 3: the sexing of the chicks then enables the classification of these categories, i.e. the association with each category of one of the following pieces of information: "male embryo", "female embryo" and "clear egg or dead embryo".

The steps 1 to 3 can be reiterated on several "configuration batches". The database 109 is thus increased by the regular input of new measurements.

The decision algorithm relating to the fertility and/or sex of an egg comprises for example the following steps for each egg of a given batch ("batch to be tested"):
   Step a: a Raman spectrum (spectral response of the shell according to the technique described above with reference to FIGS. 3 and 4) is read on the egg to be tested;
   Step b: the quality of the measurement is evaluated on each determining zone (cf. definition further above), for example by computing the first derivative and the second derivative of the spectrum. The quality criterion is for example computed by taking account of the dynamics of measurement represented by the maximum deviation of the measurement in the zone, the variability of the data represented by the number of slope inversions in the zone given by the first derivative and the noise level given by the standard deviation of the second derivative in the zone;
   Step c: if the quality criterion is sufficient, the spectrum is compared by correlation, on the determining zones, with the different reference spectra of the database in order to determine their category and therefore their gender ("male embryo", "female embryo" and "clear egg or dead embryo").

Figure 5:
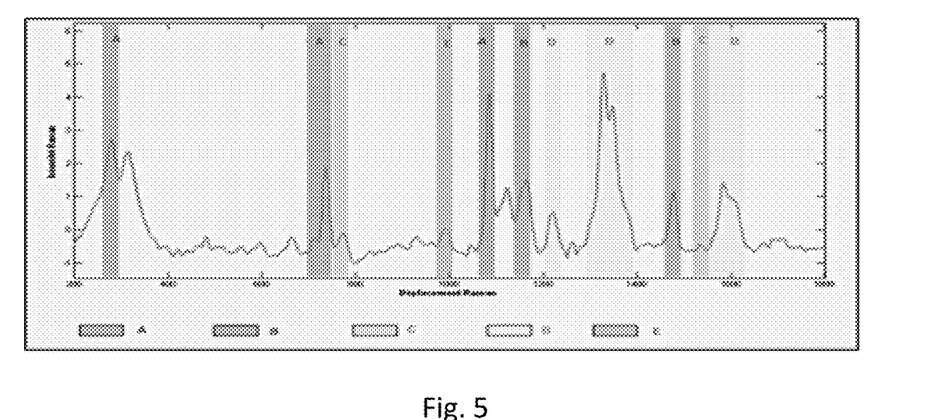
FIG. 5 illustrates an example of a spectrum obtained with the device of FIG. 3.

FIG. 5 illustrates an example of a spectral response (spectrum) specific to the shell 10 obtained with the device 100 of FIG. 3. This spectrum represents a combination of responses of the substances 50 present on the surface and/or inside the shell 10 of the egg 1. The comparison of these spectra with the spectra of biological samples referred to in the literature enables an association of the presence of certain compounds or molecules with the visible bands. For example, the A bands are associated with calcium carbonate, the B bands with the carotenoids, the C bands with DNA, the D bands with lipid or protein structures and the E bands with phenylalanine. The comparison with the database is made on these bands but also on intermediate bands where the signals are weaker such as in the 800 to 900 $cm^{-1}$ zone.

In one variant of this embodiment, the length d2 of the end-piece 104 is cal calculated so that the focal point 113 is situated in one of the layers of the shell 10. In other words, the presence of the discriminant substances 50 is sought no longer on the external surface of the external layer 16 of the shell 10 but inside one of the layers (11, 12, 13, 14, 15 and 16) forming the shell 10.

6.3 Description of a Second Embodiment

Figure 6:
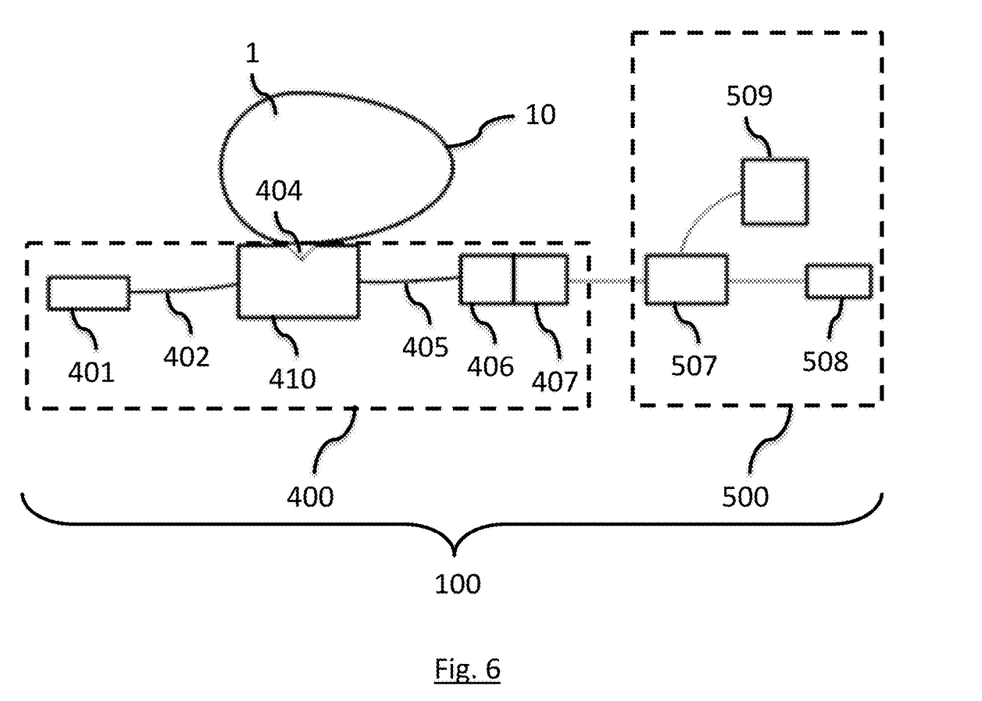
FIG. 6 presents a device for determining the fertility and/or sex of an egg according to a second embodiment of the invention.

FIG. 6 illustrates a second embodiment in which the fertility/sex of the egg are determined by means of attenuated total reflection infrared spectroscopy, known as "ATR spectroscopy".

In this second embodiment, the device 100 comprises:
  means 400 for obtaining a spectral response from at least one portion of at least one layer of the shell 10 of an egg 1. These means 400 comprise a light source 401, a first optical fiber 402, a probe 410, crystal 404, a second optical fiber 405, a spectrometer 406 and processing means 407;
  means 500 for determining the fertility and/or the sex of the egg 1 according to the spectral response specific to the shell 10. These means 500 comprise a computer 507, a database 509 and a display device 508.

The light source 401 is a polychromatic source, such as for example a carbon dioxide laser or heated silicon carbide filaments capable of providing an incident light signal, the wave lengths of which are situated in the infrared or the near infrared.

The probe 410 and the crystal 404 together form focusing means. The first optical fiber 402 is intended to transmit the incident light signal to the probe 410.

The probe 410 is an ATR (attenuated total reflection) type probe and comprises a crystal 404 transparent to infrared rays. The crystal 404 has a high reflection/refraction index or in any case a reflection/refraction index that is higher than the refraction index of the sample (here, the shell 10 of the egg 1).

The crystal 404 is meant to come into contact with the eggshell 10 and therefore enable the probe 410 to be situated at a constant distance from the egg 1.

Figure 7:
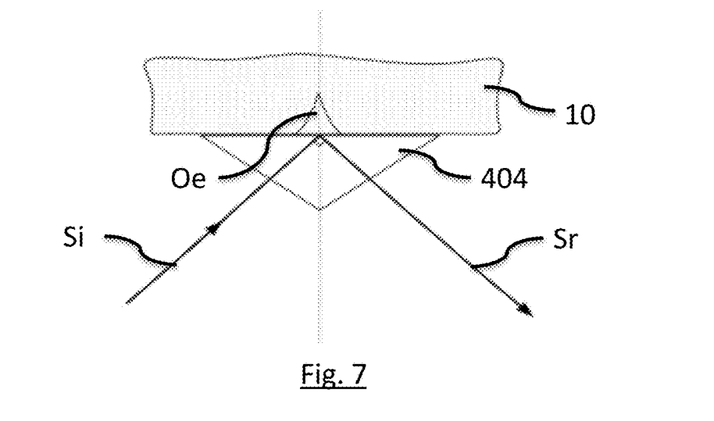
FIG. 7 is a detailed view of the operation of the probe of the device of FIG. 6.

As illustrated in FIGS. 6 and 7, the incident light signal Si is transmitted by the first optical fiber 402 to the probe 410. The incident light signal Si passes through the crystal and is in theory totally reflected by the extremity of the crystal. The reflected light signals Si is then transmitted by means of the second optical fiber 405 towards the spectrometer 406.

However, in practice this phenomenon of reflection is disturbed by the formation of an evanescent wave Oe which is created during contact between the incident light signal Si and the shell 10. Indeed, the incident light signal Si is partly absorbed by the shell 10 thus attenuating the reflected light signal Sr.

The spectral response obtained by the spectrometer 406 must then be processed by the processing means 407 in order to obtain the spectral response specific to the shell 10, i.e. the spectral response Roe of the evanescent wave Oe.

Since the spectral response RSi of the incident light signal Si and the spectral response RSr of the reflected light signal Sr are known, it is enough to deduce the spectral response Roe of the evanescent wave Oe. To this end, it is enough to subtract the spectral response of the reflected signal from the spectral response of the incident signal thus:

$$ROe = RSi - RSr$$

The spectral response ROe of the evanescent wave Oe is equivalent to/representative of the spectral response of the shell 10.

The processing means 407 then provide the spectral response, specific to the shell, to the means 500 for determining the fertility and/or the sex of the egg 1.

Within the means 500 for determining fertility and/or the sex of the egg 1, the computer 507 and the database 509 form comparison means. These means make it possible to exploit the spectral response transmitted by the processing means 407 and compare it with a library of reference spectral responses. This comparison relates either to the amplitude of one or more lines of the spectral response or to the aspect of the entire spectral response.

This comparison enables detection of the discriminant chemical substances present on the surface of the shell 10 in order to determine the fertility and/or the sex of the egg 1.

The display unit 508 is used to display the spectral response specific to the shell as well as the result of the comparison of this spectral response with the database of reference spectral responses.

More generally, the computer 507, the database 509 and the display unit 507 have a structure and an operation identical to that of the computer 107, the database 109 and the display unit 108 described in greater detail with reference to the first embodiment.

At least one embodiment of the present disclosure overcomes the different drawbacks of the prior art.

More specifically, at least one embodiment provides a technique for determining the fertility and/or sex of an egg that is non-invasive (with no penetration of the shell by any tool or removal of a sample from the egg) and simpler to implement and therefore easier to use on an industrial scale than the fourth prior-art technique described here above.

At least one embodiment provides a technique of this kind that is reliable.

Although the present disclosure has been described with reference to one or more examples, workers skilled in the art will recognize that changes may be made in form and detail without departing from the scope of the disclosure and/or the appended claims.

What is claimed is:

1. A non-invasive device for determining fertility and/or sex of an egg comprising a shell, wherein the device comprises:
  means for obtaining a spectral response, specific to the shell, to an incident light signal, comprising a focusing element configured to focus said incident light signal on a surface portion and/or an internal portion of at least one layer of the shell, and
  means for determining the fertility and/or sex of the egg as a function of said spectral response specific to the shell.

2. The device according to claim 1, wherein the incident light signal comprises at least one wavelength ranging from 200 to 1100 nm.

3. The device according to claim 1, wherein the focusing element is adapted to focusing the incident light signal on a portion of the external surface of an external layer of the shell.

4. The device according to claim 3, wherein the focusing element comprises a probe having a focusing distance D relative to a lens and an end-piece, a first extremity of which is fixedly attached to the probe and placed at a distance d1 from the lens and a second extremity of which is intended to be in contact with the egg, the end-piece having a distance d2 between the first and second extremities with d2=D−d1.

5. The device according to claim 1, wherein the means for obtaining the spectral response comprise a probe configured to transmit the incident light signal towards the egg, and to receive, at a zero angle of reflection, a reflected light signal resulting from a reflection by the egg of the incident light signal.

6. The device according to claim 5, wherein the probe is a Raman type probe.

7. The device according to claim 1, wherein the means for obtaining the spectral response specific to the shell comprise:
- an attenuated total reflection probe comprising a crystal that receives an incident light signal and generates a reflected light signal;
- a spectrometer that recovers the reflected light signal generated by said probe, and
- a processor configured to obtain the spectral response specific to the shell as a function of said incident light signal and of said reflected light signal.

8. The device according to claim 1, wherein the means for determining the fertility and/or sex of the egg comprise means for comparing the spectral response obtained with at least one reference spectral response.

9. The device according to claim 8, wherein said at least one reference spectral response belongs to the group consisting of:
- a first reference spectral response for non-fertilized eggs;
- a second reference spectral response for fertilized eggs containing dead embryos;
- a third reference spectral response for fertilized eggs containing male embryos; and
- a fourth reference spectral response for fertilized eggs containing female embryos.

10. A non-invasive method for determining the fertility and/or sex of an egg comprising a shell, the method comprising:
- focusing, by a device, an incident light signal from a light source onto a surface portion and/or an internal portion of at least one layer of the shell and obtaining a spectral response specific to the shell; and
- determining, by the device, the fertility and/or sex of the egg as a function of the spectral response obtained, specific to the shell.

* * * * *